(12) United States Patent
MacDonnell et al.

(10) Patent No.: US 11,666,893 B1
(45) Date of Patent: *Jun. 6, 2023

(54) METHODS FOR PREPARATION AND USE OF LIQUID SYNTHESIS CATALYSTS

(71) Applicant: Board of Regents, The University of Texas System, Austin, TX (US)

(72) Inventors: Frederick M. MacDonnell, Austin, TX (US); Brian H. Dennis, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/393,152

(22) Filed: Aug. 3, 2021

Related U.S. Application Data

(63) Continuation of application No. 16/528,124, filed on Jul. 31, 2019, now Pat. No. 11,110,438.

(60) Provisional application No. 62/712,547, filed on Jul. 31, 2018.

(51) Int. Cl.
| | | |
|---|---|---|
| *B01J 23/89* | (2006.01) | |
| *B01J 21/08* | (2006.01) | |
| *B01J 35/02* | (2006.01) | |
| *C07C 1/04* | (2006.01) | |
| *B01J 37/02* | (2006.01) | |
| *B01J 37/08* | (2006.01) | |

(52) U.S. Cl.
CPC .......... *B01J 23/8913* (2013.01); *B01J 21/08* (2013.01); *B01J 35/026* (2013.01); *B01J 37/0205* (2013.01); *B01J 37/0207* (2013.01); *B01J 37/0236* (2013.01); *B01J 37/088* (2013.01); *C07C 1/0435* (2013.01)

(58) Field of Classification Search
CPC ........ B01J 35/026; B01J 37/088; B01J 23/75; B01J 37/0242; B01J 35/002; B01J 37/08; B01J 23/8913; B01J 37/0207; B01J 21/08; B01J 37/0236; B01J 37/18; B01J 37/0205; B01J 35/006
See application file for complete search history.

(56) References Cited

U.S. PATENT DOCUMENTS

2017/0304807 A1* 10/2017 Decottignies .......... B01J 23/462

OTHER PUBLICATIONS

Hong et al., Speciation of Ruthenium as a reduction promoter of silica-supported Co catalyst, (ACS catalysis 2015, 5, 1273-1282).*

* cited by examiner

*Primary Examiner* — Jafar F Parsa
(74) *Attorney, Agent, or Firm* — AdamsIP, LLC; James Adams; Stephen Thompson

(57) ABSTRACT

Described herein are catalysts relating to liquid synthesis, methods of their preparation, and methods of their use. In an embodiment according to the present disclosure, a method of producing a catalyst for liquid synthesis comprises: providing a silica oxide support; pretreating the silica oxide support to remove air and moisture; impregnating the pretreated silica oxide support with cobalt from a cobalt source using a cobalt impregnation method; and calcinating the impregnated silica oxide support in an oven with a temperature ramping profile, wherein the calcinating comprises feeding air into the oven.

17 Claims, 14 Drawing Sheets

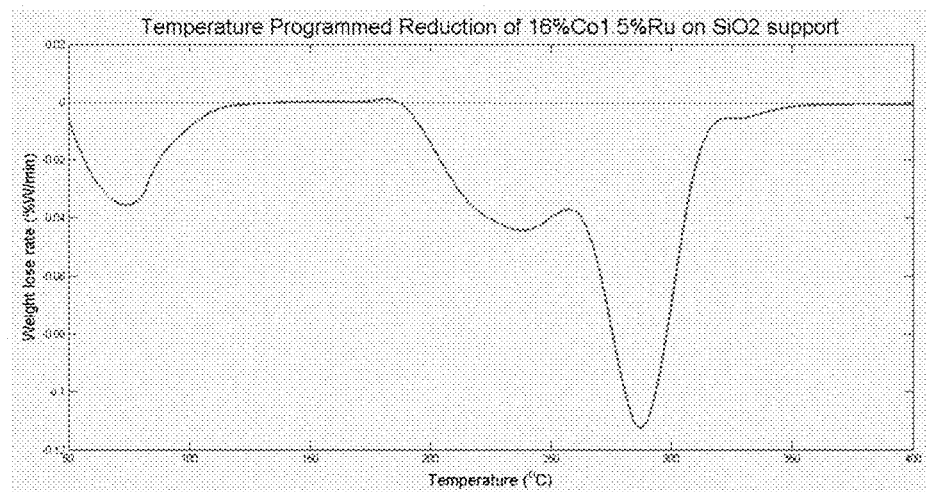
FIG. 3
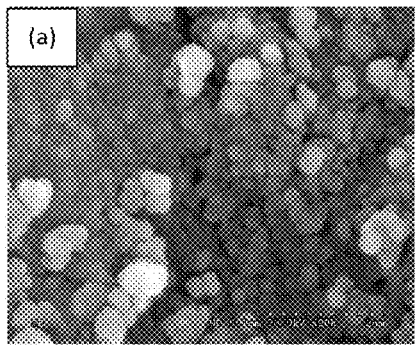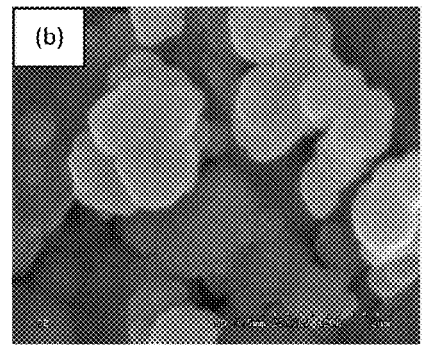
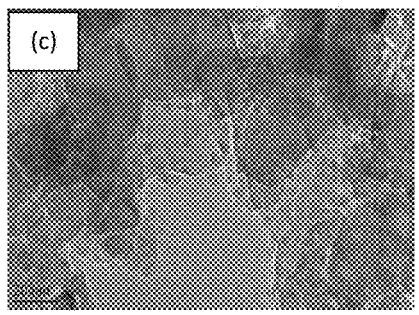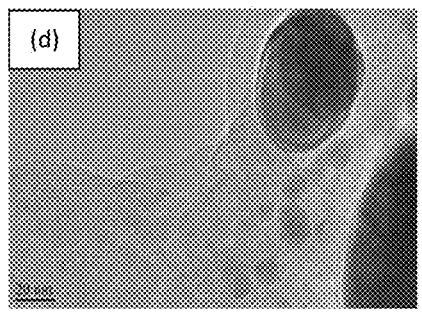
FIG. 4A  FIG. 4B
FIG. 4C  FIG. 4D

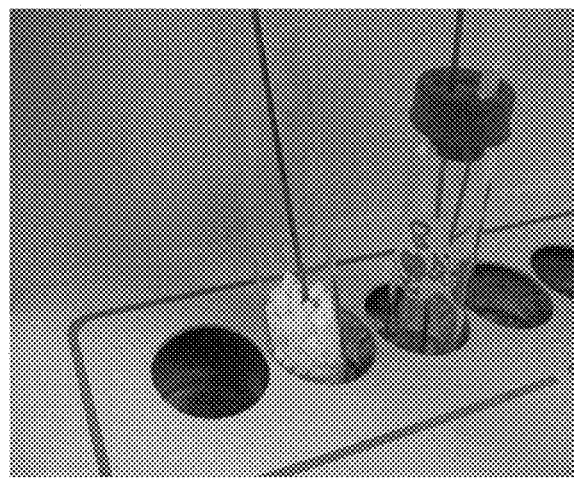
FIG. 7
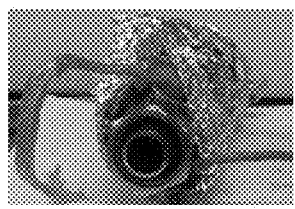 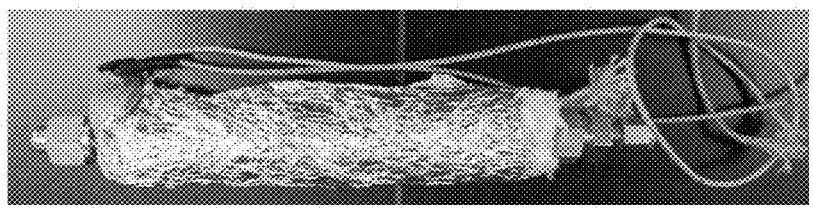
FIG. 8A              FIG. 8B (a)

(b)

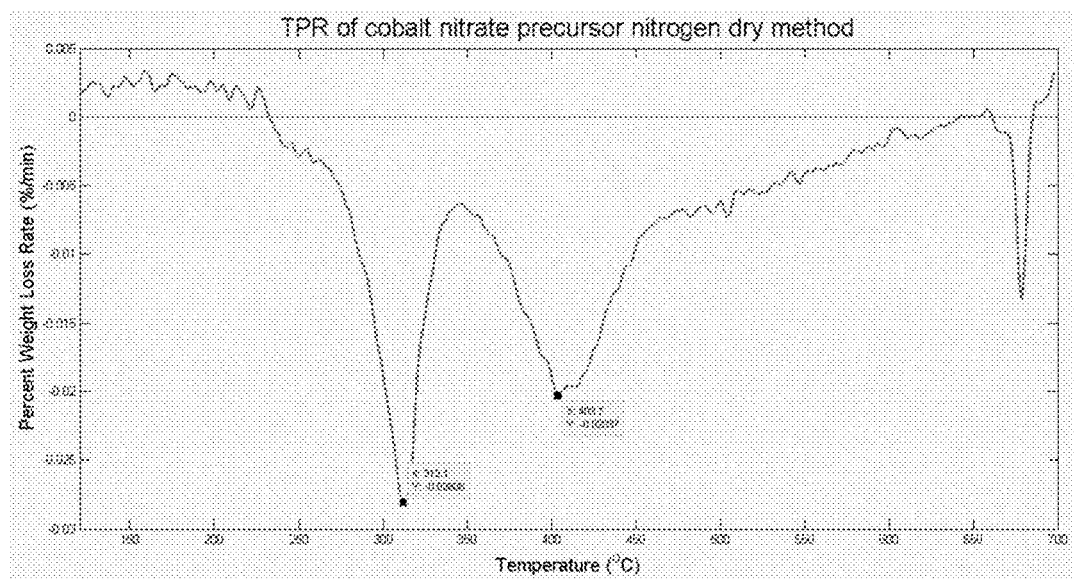
FIG. 11
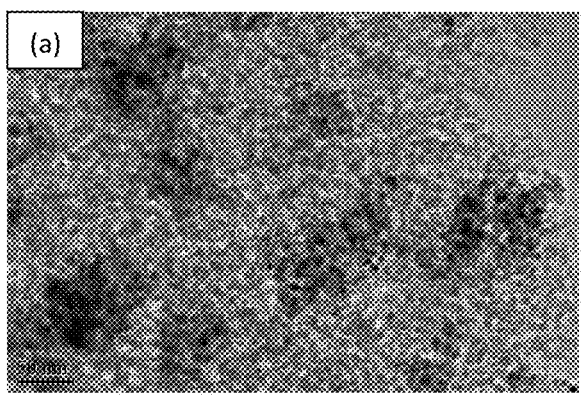 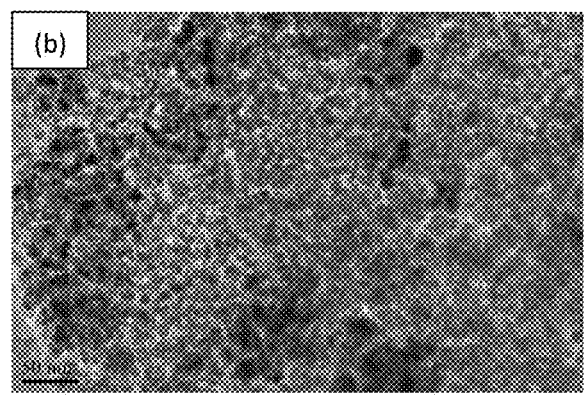
FIG. 12A　　　　　　　　　　　FIG. 12B

000
METHODS FOR PREPARATION AND USE OF LIQUID SYNTHESIS CATALYSTS

CROSS REFERENCE TO RELATED APPLICATIONS

This application is a continuation application of U.S. patent application Ser. No. 16/528,124, filed on Jul. 31, 2019, which claims priority to U.S. Provisional Patent Application No. 62/712,547, filed on Jul. 31, 2018, both of which are entitled "METHODS FOR PREPARATION AND USE OF LIQUID SYNTHESIS CATALYSTS", which applications are entirely incorporated herein by reference.

TECHNICAL FIELD

The present disclosure generally relates to catalysts of liquid synthesis, their methods of preparation, and methods of their use.

BACKGROUND

Liquid synthesis catalysts for the production of liquids, such as alcohols and hydrocarbons, previously have not been optimal due to issues such as dispersion of metals (such as cobalt) throughout the catalyst as well as cluster size. Liquid synthesis catalysts also often require high to extreme operating pressures for optimal results, leading to expensive operation and expensive reaction vessel materials. Furthermore, previous liquid synthesis catalysts generate a wax product which requires further processing for the desired liquid-phase product.

Accordingly, there is a need to address the aforementioned deficiencies and inadequacies.

SUMMARY

In aspects of the present disclosure, described herein are methods of producing a catalyst for liquid synthesis. In an embodiment, a method of producing a catalyst for liquid synthesis comprises: providing a silica oxide support; pretreating the silica oxide support to remove air and moisture; impregnating the pretreated silica oxide support with cobalt from a cobalt source using a cobalt impregnation method; and calcinating the impregnated silica oxide support in an oven with a temperature ramping profile, wherein the calcinating comprises feeding air into the oven. In an embodiment, the silica oxide support can have a surface area of about 200 m$^2$/g to about 400 m$^2$/g. In an embodiment, the silica oxide support can have a crush strength of about 10 pounds to about 30 pounds. In an embodiment, the silica oxide support can have a pore volume of about 0.9 Hg, cc/g to about 1.5 Hg, cc/g. In an embodiment, the silica oxide support comprises silica oxide pellets. In an embodiment, the silica oxide pellets can be cylindrical and have a dimension (for example length, width, or diameter) of about 2 mm to about 4 mm. In an embodiment, the silica oxide pellets can have a packing density of about 20 lbs/ft$^3$ to about 40 lbs/ft$^3$. In an embodiment, the cobalt source can be cobalt nitrate or cobalt chloride. In an embodiment, the cobalt impregnation method can be incipient wet impregnation (IWI). In embodiments, methods as described herein can further comprise impregnating the cobalt-impregnated support with ruthenium (Ru) from a Ru source with a Ru impregnation method before calcinating. In an embodiment, the ruthenium impregnation method can be incipient wet impregnation (IWI). In an embodiment, the Ru source can be ruthenium chloride or ruthenium nitrate.

In embodiments according to the present disclosure, methods as described herein can further comprise drying the impregnated silica oxide support with N$_2$ gas (or air) at a temperature of about 90° C. to about 130° C. before calcinating. In an embodiment, the pretreating can be at 90° C. to about 120° C. In an embodiment, the pretreating can be done in the presence of an inert gas.

In an embodiment, the temperature ramping profile can comprise: ramping from a temperature of about 25° C. to about 100° C. at a rate of about 10° C./min; holding at a temperature of about 100° C. for about 30 minutes; ramping from a temperature of about 100° C. to about 400° C. at a rate of about 10° C./min; and holding at a temperature of about 400° C. for about 5 hours.

Described herein are catalyst products of any of the methods of producing a catalyst as described herein.

In aspects of the present disclosure, described herein are methods of using a liquid synthesis catalyst. In an embodiment, a method of using a liquid synthesis catalyst as described herein can comprise: positioning a liquid synthesis catalyst in a reactor; bedding and packing the liquid synthesis catalyst in the reactor; reducing the liquid synthesis catalyst with H$_2$ gas; cooling the reactor to about 110° C. to about 160° C. while purging with H$_2$ gas and increasing the reactor pressure to a set pressure point; activating the liquid synthesis catalyst by introducing a gas stream into the reactor, wherein the gas stream comprises H$_2$ gas and CO from a CO source at a molar ratio of 2:1 H$_2$ to CO; and collecting the reaction products in a reaction vessel.

In an embodiment, the bedding and packing can comprise diluting the liquid synthesis catalyst with quartz and holding the mixture in a position in the reactor. In an embodiment, the set pressure point can be about 150 psi to about 300 psig. In embodiments of methods as described herein, methods can further comprise separating the collected reaction products. In an embodiment, the FTS catalyst is a catalyst product of any methods as described herein.

Described herein are reaction products of any of the methods of use of catalysts as described herein.

Described herein are methods of producing catalysts for liquid synthesis. In an embodiment according to the present disclosure, a method of producing a catalyst for liquid synthesis comprises: providing a silica oxide support; pretreating the silica oxide support to remove air and moisture; impregnating the pretreated silica oxide support with cobalt from a cobalt source using a cobalt impregnation method; and calcinating the impregnated silica oxide support in an oven with a temperature ramping profile, wherein the calcinating comprises feeding air into the oven.

In an embodiment of a method according to the present disclosure, the silica oxide support can comprise silica oxide pellets.

In an embodiment of a method according to the present disclosure, the cobalt source can be cobalt nitrate or cobalt chloride.

In an embodiment of a method according to the present disclosure, the cobalt impregnation method can be incipient wet impregnation (IWI).

In an embodiment of a method according to the present disclosure, methods as described herein can further comprise impregnating the cobalt-impregnated support with ruthenium (Ru) from a Ru source with an Ru impregnation method before calcinating.

In an embodiment of a method according to the present disclosure, the ruthenium impregnation method can be IWI.

In an embodiment of a method according to the present disclosure, the Ru source can be ruthenium chloride or ruthenium nitrate.

In an embodiment of a method according to the present disclosure, methods as described herein can further comprise drying the impregnated silica oxide support with $N_2$ gas at a temperature of about 90° C. or about 110° C. before calcinating.

In an embodiment of a method according to the present disclosure, methods as described herein can further comprise drying the impregnated silica oxide support with air at a temperature of about 90° C. or about 110° C. before calcinating.

In an embodiment of a method according to the present disclosure, the pretreating can be at 90° C. to about 120° C.

In an embodiment of a method according to the present disclosure, the pretreating can be done in the presence of an inert gas.

In an embodiment of a method according to the present disclosure, the temperature ramping profile can comprise: ramping from a temperature of about 25° C. to about 100° C. at a rate of about 10° C./min; holding at a temperature of about 100° C. for about 30 minutes; ramping from a temperature of about 100° C. to about 400° C. at a rate of about 10° C./min; and holding at a temperature of about 400° C. for about 5 hours;

Also described herein are embodiments of catalysts produced by embodiments of methods as described herein.

Also described herein are embodiments of methods of using a liquid synthesis catalyst. In an embodiment, a method of using a liquid synthesis catalyst as described herein can comprise: positioning a liquid synthesis catalyst in a reactor; bedding and packing the liquid synthesis catalyst in the reactor; reducing the liquid synthesis catalyst with $H_2$ gas; cooling the reactor to about 150° C. while purging with $H_2$ gas and increasing the reactor pressure to a set pressure point; activating the liquid synthesis catalyst by introducing a gas stream into the reactor, wherein the gas stream comprises $H_2$ gas and CO from a CO source at a molar ratio of 2:1 $H_2$ to CO; and collecting the reaction products in a reaction vessel.

In an embodiment of a method according to the present disclosure, the bedding and packing comprises diluting the liquid synthesis catalyst with quartz and holding the mixture in a position in the reactor.

In an embodiment of a method according to the present disclosure, the set pressure point is about 300 psig.

In embodiments of methods of using embodiments of liquid synthesis catalysts according to the present disclosure, embodiments of methods as described herein can further comprise separating the collected reaction products.

In embodiments of methods according to the present disclosure, the FTS catalyst is a catalyst product of any method of production as described herein.

Also described herein are reaction products created by any of the embodiments of methods of using embodiments of liquid synthesis catalysts as described herein.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3 is a graph illustrating the rate of mass loss as a function of temperature in TPR run of calcined precatalyst 16% Co1.5% Ru/SiO$_2$ catalyst (UTA-1) with temperature ramp 1° C./min from 100° C. to 900° C. under 20 ml/min of mixed gas (3% $H_2$ 97% $N_2$) flow rate.

FIGS. 4A-4D are electron micrographs showing an embodiment of a catalyst as described herein, UTA-1. FIG. 4A is an scanning electron microscope (SEM) image of spent catalyst showing clumps of SiO$_2$ particles size 0.4 µm to 2 µm; FIG. 4B is an SEM image of spent catalyst showing the sintering of the SiO$_2$ particles from 0.4 µm to 2 µ to 1 µm to 4 µm; FIG. 4C is a transmission electron microscope (TEM) image of reduced catalyst showing the uniform distributed of cobalt nanoparticle between 5-10 nm; and FIG. 4D is a TEM of spent catalyst showed the sintering of cobalt nanoparticles size 50-100 nm.

FIG. 7 is a photograph showing silica oxide support pretreated in a degas machine supplied with $N_2$ gas.

FIGS. 8A-8B are photographs showing a stainless steel tube furnace wrapped with heating element and insulator.

FIG. 9A shows after impregnated with cobalt nitrate and dried, and FIG. 9B after calcine.

FIG. 10A shows the aqueous phase product and FIG. 10B the oil product.

FIG. 11 is a graph showing rate of mass loss as a function of temperature in TPR run of calcined precatalyst 16% Co/SiO$_2$ with $N_2$ dry method (UTA-2). TPR was done under temperature ramp 1° C./min from 100° C. to 900° C. under 20 ml/min of mixed gas (3% $H_2$ 97% $N_2$) flow rate.

FIGS. 12A-12B are TEM images showing the comparison of cobalt clusters size of the 16% Co/SiO$_2$ with different drying methods. FIG. 12A shows cobalt agglomerate around 80-100 nm with air dry method and FIG. 12B cobalt uniform disperse over SiO$_2$ support by using $N_2$ dry method (black zone).

DETAILED DESCRIPTION

Figure 1:
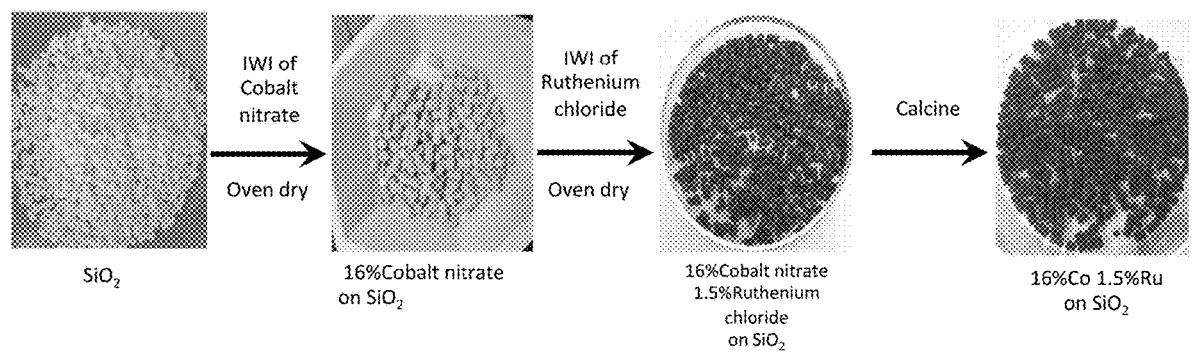
FIG. 1 is a schematic of an embodiment of the preparation of an embodiment of a catalyst for liquid synthesis.

Described below are various embodiments of catalysts, liquid synthesis catalysts, Fischer-Tropsch synthesis catalysts, methods of making, and methods of use. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

DISCUSSION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medical imaging, physics, mechanical engineering, biochemistry, cellular biology, cancer biology and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

Definitions

The terms "reformation" and "reforming", as used interchangeably herein, refer to the process of converting a hydrocarbon to methane, lower hydrocarbons, higher hydrocarbons, oxygenates, hydrogen gas, water, carbon dioxide, carbon monoxide, and combinations thereof. The process can include converting at least about 20 mol. %, 30 mol. %, 40 mol. %, 50 mol. %, 60 mol. %, 70 mol. %, 80 mol. %, 85 mol. %, 90 mol. %, 95 mol. %, 98 mol. %, or more of the hydrocarbon into methane, lower hydrocarbons, higher hydrocarbons, hydrogen gas, water, carbon dioxide, carbon monoxide, or a combination thereof. Reformation can convert hydrocarbons into a value added hydrocarbon mixture such as ethylene, naphtha, gasoline, kerosene, or diesel oil.

The term "hydrocarbon", as used herein, refers generally to any saturated on unsaturated compound including at least carbon and hydrogen and, optionally, one or more additional atoms. Additional atoms can include oxygen, nitrogen, sulfur, or other heteroatoms. In some embodiments the hydrocarbon includes only carbon and hydrogen. The hydrocarbon can be a pure hydrocarbon, meaning the hydrocarbon is made of only carbon and hydrogen atoms. The term "hydrocarbon" includes saturated aliphatic groups (i.e., an alkane), including straight-chain alkanes, branched-chain alkanes, cycloalkanes, alkyl-substituted cycloalkanes, and cycloalkyl-substituted alkanes. In preferred embodiments, a straight chain or branched chain alkane has 30 or fewer carbon atoms in its backbone (e.g., $C_1$-$C_{30}$ for straight chains, and $C_3$-$C_{30}$ for branched chains), preferably 20 or fewer, more preferably 15 or fewer, most preferably 10 or fewer. Likewise, preferred cycloalkanes have 3-10 carbon atoms in their ring structure, and more preferably have 5, 6, or 7 carbons in the ring structure. The term "hydrocarbon" (or "lower hydrocarbon") as used throughout the specification, examples, and claims is intended to include both "unsubstituted alkanes" and "substituted alkanes", the latter of which refers to alkanes having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

The term "lower hydrocarbon", as used herein, refers generally to a hydrocarbon having a lower overall number of carbon atoms or a lower overall molecular weight as compared to a reference hydrocarbon. Unless the number of carbons is otherwise specified, "lower hydrocarbon" as used herein includes "lower alkanes", "lower alkenes", and "lower alkynes" having from one to ten carbons, from one to six carbon atoms, or from one to four carbon atoms in its backbone structure. The lower hydrocarbon can include ethane, ethene, propane, and propene, heptane, octane, optionally including one or more substituents or heteroatoms, as well as derivatives thereof.

The term "higher hydrocarbon", as used herein, refers generally to a hydrocarbon having a higher overall number of carbon atoms or a higher overall molecular weight as compared to a reference hydrocarbon. Unless the number of carbons is otherwise specified, "high hydrocarbon" as used herein can include "higher alkanes", "higher alkenes", and "higher alkynes" having from two to twenty carbon atoms, four to twenty carbon atoms, four to eighteen carbon atoms, six to eighteen carbon atoms, or from ten to eighteen carbon atoms. Higher hydrocarbons can include alkanes and cycloalkanes having from five to twelve carbon atoms and commonly found in petrol. Higher hydrocarbons can include alkanes have more than twelve carbon atoms, e.g. from twelve to thirty or from twelve to twenty carbon atoms and commonly found in diesel oil.

The term "oxygenate", as used herein, refers to the corresponding hydrocarbon, lower hydrocarbon, or higher hydrocarbon wherein one or more hydrogen atoms has been substituted with an —OH substituent to form an alcohol.

The term "naphtha", as used herein, refers to a mixture of hydrocarbons containing predominately hydrocarbons having from five to ten carbon atoms. Naphtha can have a boiling temperature from 30° C. to 200° C., from 40° C. to 190° C., or from 50° C. to 180° C. Naphtha can include "light naphtha" or "heavy naphtha". The term "light naphtha" refers to mixtures of hydrocarbons containing predominately hydrocarbons have five or six carbon atoms and having a boiling point from 30° C. to 90° C. or from 30° to 80° C. The term "heavy naphtha" refers to mixtures of hydrocarbons containing predominately hydrocarbons having from six to twelve, from seven to twelve, or from eight to ten carbon atoms and having a boiling point from 90° C. to 200° C., from 100° C. to 200° C., or from 120° C. to 180° C.

The term "gasoline", as used herein, refers to a mixture of hydrocarbons containing predominately hydrocarbons having from five to twelve or from six to ten carbon atoms and a boiling point from 25° C. to 200° C. or from 50° C. to 150° C.

The term "kerosene", as used herein, refers to a mixture of hydrocarbons containing predominately hydrocarbons having from twelve to fifteen carbon atoms and a boiling point from 200° C. to 300° C.

The terms "diesel" and "diesel oil", as used interchangeably herein, refer to mixture of hydrocarbons containing predominately hydrocarbons having from eleven to twenty carbon atoms or from twelve to eighteen carbon atoms. Diesel oil can have a boiling point from 150° C. to 400° C. or from 175° C. to 350° C.

Suitable heteroatoms can include, but are not limited to, 0, N, Si, P, Se, B, and S, wherein the phosphorous and sulfur atoms are optionally oxidized, and the nitrogen heteroatom is optionally quaternized. Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14, 1-12, or 1-6 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted C3-C20 cyclic, heterocyclic, substituted heterocyclic, amino acid, peptide, and polypeptide groups.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

The terms "syngas" and "synthesis gas", as used interchangeably herein, refer to a gas mixture containing mostly hydrogen ($H_2$) gas and carbon monoxide (CO) gas and about 20 mol-%, 15 mol-%, 12 mol-%, 10 mol-%, 8 mol-%, 6 mol-%, 5 mol-%, or less of other components such as molecular oxygen ($O_2$), carbon dioxide ($CO_2$) gas and gases of lower hydrocarbons. The syngas can have about 5 mol-%, 3 mol-%, 2 mol-%, 1 mol-%, or 0.5 mol-% of molecular oxygen. The syngas can have about 15 mol-%, 10 mol-%, 8 mol-%, 6 mol-%, 5 mol-%, 4 mol-%, 3 mol-%, 2 mol-%, or less of carbon dioxide.

The term "high melting point", when referring to a metal or metal alloy herein, means a metal or metal alloy having a melting point that is about 800° C., 900° C., 1000° C., 1200° C., 1500° C., 2000° C., 2500° C. or higher.

By "chemically feasible" is meant a bonding arrangement or a compound where the generally understood rules of organic structure are not violated. The structures disclosed herein, in all of their embodiments are intended to include only "chemically feasible" structures, and any recited structures that are not chemically feasible, for example in a structure shown with variable atoms or groups, are not intended to be disclosed or claimed herein.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded.

As used herein, an "analog", or "analogue" of a chemical compound is a compound that, by way of example, resembles another in structure but is not necessarily an isomer (e.g., 5-fluorouracil is an analog of thymine).

As used herein, a "derivative" of a compound refers to a chemical compound that may be produced from another compound of similar structure in one or more steps, as in replacement of H by an alkyl, acyl, or amino group.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon.

As used herein, "alkyl" or "alkyl group" refers to a saturated aliphatic hydrocarbon radical which can be straight or branched, having 1 to 40, 1 to 20, 1 to 10, or 1 to 5 carbon atoms, where the stated range of carbon atoms includes each intervening integer individually, as well as sub-ranges. Examples of alkanes include, but are not limited to methyl, ethyl, n-propyl, i-propyl, n-butyl, s-butyl, t-butyl, n-pentyl, and s-pentyl. Reference to "alkyl" or "alkyl group" includes unsubstituted and substituted forms of the hydrocarbon group.

As used herein, "alkene" refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethene, propene, and the like. Reference to "alkene" includes unsubstituted and substituted forms of the hydrocarbon.

As used herein, "alkenyl" or "alkenyl group" refers to an aliphatic hydrocarbon radical which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to "alkyl" or "alkyl group" includes unsubstituted and substituted forms of the hydrocarbon group.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon.

As used herein, "alkynyl" or "alkynyl group" refers to straight or branched chain hydrocarbon groups having 2 to 40, 2 to 20, 2 to 10, or 2 to 5 carbon atoms and at least one triple carbon to carbon bond, such as ethynyl. Reference to "alkynyl" or "alkynyl group" includes unsubstituted and substituted forms of the hydrocarbon group.

As used herein, "aromatic" refers to a monocyclic or multicyclic ring system of 6 to 20 or 6 to 10 carbon atoms having alternating double and single bonds between carbon atoms. Exemplary aromatic groups include benzene, naphthalene, and the like. Reference to "aromatic" includes unsubstituted and substituted forms of the hydrocarbon.

As used herein, "aryl" or "aryl group" refers to an aromatic monocyclic or multicyclic ring system of 6 to 20 or 6 to 10 carbon atoms. The aryl is optionally substituted with one or more $C_1$-$C_{20}$ alkyl, alkylene, alkoxy, or haloalkyl groups. Exemplary aryl groups include phenyl or naphthyl, or substituted phenyl or substituted naphthyl. Reference to "aryl" or "aryl group" includes unsubstituted and substituted forms of the hydrocarbon group.

The term "substituted," as in "substituted alkyl", "substituted aryl," "substituted heteroaryl" and the like, means that the substituted group may contain in place of one or more hydrogens a group such as alkyl, hydroxy, amino, halo, trifluoromethyl, cyano, alkoxy, alkylthio, or carboxy.

As used herein, "halo", "halogen", "halide", or "halogen radical" refers to a fluorine, chlorine, bromine, iodine, and astatine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, "cyclic" hydrocarbon refers to any stable 4, 5, 6, 7, 8, 9, 10, 11, or 12 membered, (unless the number of members is otherwise recited), monocyclic, bicyclic, or tricyclic cyclic ring.

As used herein, "heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which includes carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)2, and N—O). The heterocycle may be attached to its pendant group at any heteroatom or carbon atom that results in a stable structure. The heterocycles described herein may be substituted on carbon or on a heteroatom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)2, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring).

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DESCRIPTION

The present disclosure is directed to catalysts relating to liquid synthesis, Fischer-Tropsch synthesis, methods of their preparation, and methods of their use.

Methods for producing liquid synthesis catalysts as described herein can lead to better dispersion of metal elements within the catalyst compared to previous methods. Methods of using liquid synthesis catalysts as described herein involve moderate operating conditions that avoid the use of extreme temperature and/or pressure. Methods of using catalysts as described herein do not produce waxy products, and instead produce liquid products that do not require further processing to produce products in liquid state.

Described herein are methods of producing a catalyst for liquid synthesis from gas starting products. In certain embodiments, described herein are methods of producing a catalyst for Fischer-Tropsch synthesis (also referred to herein as a catalyst or FTS catalyst).

Methods as described herein can comprise: providing a silica oxide support; pretreating the silica oxide support to remove air and moisture; impregnating the pretreated silica oxide support with cobalt from a cobalt source using a cobalt impregnation method; and calcinating the impregnated silica oxide support in an oven with a temperature ramping profile, wherein the calcinating comprises feeding air into the oven.

Silica oxide supports according to the present disclosure can be silica oxide pellets. In certain aspects, the silica oxide pellets can be about 2 mm to about 4 mm cylindrical pellets (about 2 mm to about 3 mm or about 3 mm to about 4 mm).

In embodiments according to the present disclosure, silica oxide supports can have a surface area of about 200 $m^2/g$ to about 400 $m^2/g$; about 210 $m^2/g$ to about 390 $m^2/g$; about 220 $m^2/g$ to about 380 $m^2/g$; about 230 $m^2/g$ to about 370 $m^2/g$; about 240 $m^2/g$ to about 360 $m^2/g$; about 250 $m^2/g$ to about 350 $m^2/g$; about 260 $m^2/g$ to about 340 $m^2/g$; about 270 $m^2/g$ to about 330 $m^2/g$; about 280 $m^2/g$ to about 320 $m^2/g$; about 290 $m^2/g$ to about 310 $m^2/g$; or about 300 $m^2/g$. In certain embodiments, silica oxide supports can have a surface area of about 254 m 2/g.

In embodiments according to the present disclosure, silica oxide supports can have a crush strength of about 10 pounds to about 30 pounds; about 12.5 pounds to about 27.5 pounds; about 15 pounds to about 25 pounds; about 17.5 pounds to about 22.5 pounds; or about 20 pounds. In certain embodiments, silica oxide supports can have a crush strength of about 16 pounds.

In embodiments according to the present disclosure, silica oxide supports can have a packing density of about 20 $lbs/ft^3$ to about 40 $lbs/ft^3$; about 22.5 $lbs/ft^3$ to about 37.5 $lbs/ft^3$, about 25 $lbs/ft^3$ to about 35 $lbs/ft^3$; about 27.5 $lbs/ft^3$ to about 32.5 $lbs/ft^3$; or about 30 $lbs/ft^3$. In certain embodiments, silica oxide supports can have a packing density of about 25.4 $lbs/ft^3$.

In embodiments according to the present disclosure, silica oxide supports can have a pore volume of about 0.9 Hg, cc/g to about 1.5 Hg, cc/g; about 1 Hg, cc/g to about 1.4 Hg, cc/g; about 1.1 Hg, cc/g to about 1.3 Hg, cc/g; or about 1.2 Hg, cc/g. In certain embodiments, silica oxide supports can have a pore volume of about 1.04 Hg, cc/g.

In embodiments according to the present disclosure, silica oxide supports can have a pore volume of about 0.9 $lbs/ft^3$ to about 1.5 $lbs/ft^3$; about 1 $lbs/ft^3$ to about 1.4 $lbs/ft^3$; about 1.1 $lbs/ft^3$ to about 1.3 $lbs/ft^3$; or about about 1.2 $lbs/ft^3$. In certain embodiments, silica oxide supports can have a pore volume of about 1.04 $lbs/ft^3$.

In an embodiment, the silica oxide support can be comprised of about 2 mm to about 4 mm cylindrical pellets with one or more of the following properties: surface area of about 200 $m^2/g$ to about 400 $m^2/g$, crush strength of about 10 pounds to about 30 pounds, packing density of about 20 $lbs/ft^3$ to about 40 $lbs/ft^3$, total pore volume of about 0.9 Hg, cc/g to about 1.5 Hg, cc/g.

In an embodiment, the silica oxide support can be comprised of 3 mm cylindrical pellets with one or more of the following properties: surface area of about 254 m²/g, crush strength of about 16.0 lb, packing density of about 25.4 lbs/ft³, total pore volume of about 1.04 Hg, cc/g.

Cobalt sources according to the present disclosure can be a cobalt salt. In certain aspects, the cobalt salt is cobalt chloride or chloride nitrate. In an embodiment, the cobalt source is cobalt nitrate.

Methods as described herein can include a cobalt impregnation method. In an embodiment, the cobalt impregnation method is incipient wet impregnation (IWI).

Methods as described herein can further comprise impregnating the cobalt-impregnated support with ruthenium (Ru) from a Ru source with an Ru impregnation method before calcinating. The ruthenium impregnation method can be IWI. The Ru source can be a ruthenium salt. In certain aspects, the ruthenium source can be ruthenium chloride or ruthenium nitrate. In an embodiment, the Ru source is ruthenium chloride.

Methods as described herein can further comprise drying the impregnated silica oxide support with $N_2$ gas or air at a temperature of about 110° C. (or about 90° C. to about 130° C.; 112.5° C. to about 127.5° C.; 115° C. to about 125° C.; 117.5° C. to about 122.5° C.; or about 120° C.) before calcinating.

In certain aspects, the silica support is pretreated to remove air and/or moisture. In certain aspects, the pretreating is at about 90° C. to about 120° C. (or about 100° C. to about 110° C.). In certain embodiments, the pretreating is done in the presence of an inert gas. In embodiments, the inert gas is nitrogen ($N_2$), argon (Ar), or helium (He), individually or in combination.

In certain aspects, the catalyst is calcinated in an oven with a temperature ramping profile (i.e., an increase over time or a decrease over time). In embodiments, the temperature ramping profile can comprise: ramping from a temperature of about 25° C. (or about 22.5° C. to about 27.5° C., about 23.5° C. to about 26.5° C., or about 24.5° C. to about 25.5° C.) to about 100° C. (or about 90° C. to about 110° C., or about 99.5° C. to about 100.5° C.) at a rate of about 10° C./min (or about 9.9° C./min to about 10.1° C./min); holding at a temperature of about 100° C. (or about 90° C. to about 110° C., or about 99.5° C. to about 100.5° C.) for about 30 minutes (or about 25 minutes to about 35 minutes, about 27.5 to about 32.5 minutes); ramping from a temperature of about 100° c. (or about 90° C. to about 110° C., or about 99.5° C. to about 100.5° C.) to about 400° C. (or about 350° C. to about 450° C., about 360° C. to about 440° C., about 370° C. to about 430° C., about 380° C. to about 420° C., or about 390° C. to about 410° C.) at a rate of about 10° C./min; and holding at a temperature of about 400° C. (or about 350° C. to about 450° C., about 360° C. to about 440° C., about 370° C. to about 430° C., about 380° C. to about 420° C., or about 390° C. to about 410° C.) for about 5 hours (or about 4.5 hours to about 5.5 hours). In other aspects, the temperatures, ramp times, holding times, and ramp rates can vary by about ±10%.

Catalysts as described herein can be the product of any of the methods described herein.

Described herein are methods of using a liquid synthesis catalyst. Methods of use as described herein can comprise: positioning the liquid synthesis catalyst in a reactor; bedding and packing the liquid synthesis catalyst in the reactor; reducing the liquid synthesis catalyst with $H_2$ gas; cooling the reactor to about 150° C. (or about 110° C. to about 160° C.; 115° C. to about 155° C.; 120° C. to about 125° C.; 125° C. to about 150° C.; 130° C. to about 145° C.; or about 135° C.) while purging with $H_2$ gas and increasing the reactor pressure to a set pressure point; activating the liquid synthesis catalyst by introducing a gas stream into the reactor, wherein the gas stream comprises $H_2$ gas and CO from a CO source at a molar ratio of 2:1 $H_2$ to CO; and collecting the reaction products in a reaction vessel.

In an embodiment, described herein are methods of using a Fischer-Tropsch synthesis (FTS) catalyst. Methods of use as described herein can comprise: positioning the FTS catalyst in a reactor; bedding and packing the FTS catalyst in the reactor; reducing the FTS catalyst with $H_2$ gas; cooling the reactor to about 150° C. while purging with $H_2$ gas and increasing the reactor pressure to a set pressure point; activating the FTS catalyst by introducing a gas stream into the reactor, wherein the gas stream comprises $H_2$ gas and CO from a CO source at a molar ratio of 2:1 $H_2$ to CO; and collecting the reaction products in a reaction vessel.

The bedding and packing as described herein can comprise diluting the liquid synthesis catalyst with quartz and holding the mixture in a position in the reactor. The mixture can be held in place in the reactor with steel wool.

In embodiments according to the present disclosure, set pressure points according to methods as described herein can be about 150 psi to about 350 psi; 160 psi to about 340 psi; 170 psi to about 330 psi; 180 psi to about 320 psi; 190 psi to about 310 psi; 200 psi to about 300 psi; 210 psi to about 290 psi; 220 psi to about 280 psi; 230 psi to about 270 psi; 240 psi to about 260 psi; or about 250 psi. In an embodiment, set pressure points according to methods as described herein can be about 300 psig.

The collected reaction products can further be separated according to methods as described herein. The products are immiscible (a water phase and an oil phase) so the oil can be decanted. This could be done manually by hand (simply pouring the oil layer off the water layer). Separation can be accomplished continuously using a weir. The floating oil spills over the weir and can be drained. The water phase can be drained from the bottom.

Methods as described herein can utilize liquid synthesis catalysts produced by any of the methods described herein for liquid synthesis. Liquid products of synthesis methods as described herein can be alcohols or hydrocarbons. In an embodiment, liquid products comprise methanol. In an embodiment, liquid products comprise hydrocarbons.

In an embodiment, methods as described herein can utilize catalysts as described herein for Fischer-Trospch synthesis.

While embodiments of the present disclosure are described in connection with the Examples below and the corresponding text and figures, there is no intent to limit the invention to the embodiments in these descriptions. On the contrary, the intent is to cover all alternatives, modifications, and equivalents included within the spirit and scope of embodiments of the present disclosure.

EXAMPLES

Example 1

Described herein is an embodiment of the method of production for an embodiment of a catalyst for Fischer-Tropsch synthesis.

Catalyst UTA-1 Preparation

A method of preparing a Fischer-Tropsch synthesis catalyst is shown in FIG. 1, and described below:

1. Commercial silica oxide support (Product ID: SS 61138) was obtained as a gift from Saint-Gobain of Stow, OH. It had the following reported properties: 3 mm cylindrical pellets, surface area 254 m²/g, Crush strength 16.0 lb, Packing Density 25.4 lbs/ft³, Total Pore Volume 1.04 Hg, cc/g.

2. The commercial $SiO_2$ support was pretreated in the 90° C. to clear out air and moisture inside the catalyst pores overnight (15-18 h).

3. Cobalt was introduced by addition of an aqueous solution of cobalt nitrate ($Co(NO_3)_2 \cdot 6H_2O$, Alfa Aesar) to give a 16% by mass cobalt metal content on silica oxide support (0.98 $g_{Cobalt\ nitrate}/g_{Sio2}$). Specifically, cobalt nitrate was dissolved in deionized water (DI water) (0.76 $mL_{DI\ water}/g_{Sio2}$) $SiO_2$ was impregnated with cobalt nitrate solution by using the incipient wet impregnation (IWI) method. After the $SiO_2$ support was impregnated, it was left to dry in the oven at 90° C. overnight (around 15-18 h).

4. The catalyst was next impregnated with ruthenium chloride ($RuCl_3 \cdot xH_2O$, Sigma Aldrich) to give a final mass percent of Ru of 1.5% metal content on $SiO_2$ support (0.039 g ruthenium chloride/g $SiO_2$). The ruthenium chloride was dissolved in DI water (1.1 mL DI water/g $SiO_2$) and the cobalt-impregnated $SiO_2$ treated with the ruthenium chloride solution via the IWI method and left to dry in the oven at 90° C. overnight (around 15-18 h).

5. After the second drying, the impregnated catalyst was calcined in a temperature programmed oven with the following temperature ramping profile:

Temp.$_{25°\ C.}$ Temp.$_{100°\ C.}$ Ramping 10° C./min
Temp.$_{100°\ C.}$ Hold for 30 min
Temp.$_{100°\ C.}$ TeMP$_{400°\ C.}$ Ramping 10° C./min
Temp.$_{400°\ C.}$ Hold for 5 h.

During the calcination process, air was fed into the temperature programmed oven from the top side to ensure complete oxidation.

In Situ Reduction and Use of the UTA-1 FT Catalyst:

The calcined catalyst was tested in the FTS reactor to measure the selectivity and productivity. Before loading, the catalyst was diluted with quartz chips at a ratio of 2 $g_{catalyst}/2.76\ g_{quartz\ chip}$. This mixture was loaded into a ⅜ inch diameter stainless steel tubular reactor. Steel wool was used to hold the catalyst bed in place in the middle of the tube. The typical bed length in these tests is 6 in. The catalyst was then reduced at 400° C. with hydrogen gas at 1 psig and a flow rate of 100 sccm for 18 h. The now reduced catalyst was cooled from 400° C. to 150° C. and then purged with $H_2$ at a steady flow rate of 100 sccm while slowly increasing the pressure to 300 psig. After the pressure reached set point, flow rate of $H_2$ was reduced to 66.67 sccm and CO was introduced to a system with flow rate 33.33 sccm. The flow rate between $H_2$ and CO was kept constant at a ratio of 2:1. Once the flow rate between $H_2$ and CO was stable, the temperature was brought up slowly (heating rate 0.6° C./min) to 255° C. and held for the duration of the run. Temperature, inlet, and outlet flow rate, and gas products activity were monitored at all time during the synthesis.

Figure 2:
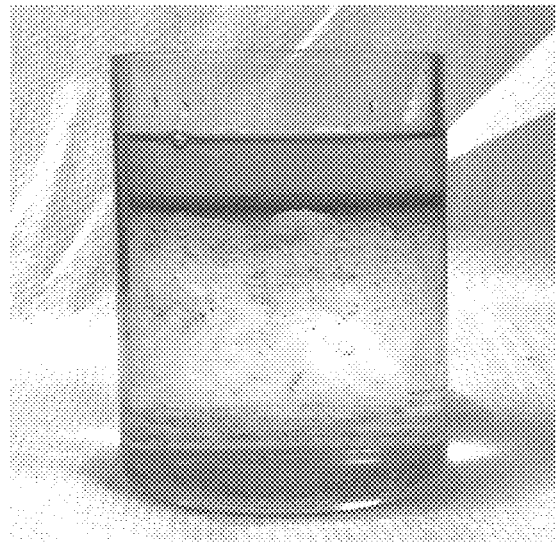
FIG. 2 is a photograph showing liquid products collected from the gas-liquid separator and liquid collector's pressure vessel before measure and analysis.

In a typical run, the FTS reactor was continuously for 5 days before shutting down. During the reaction period, the liquid products were collected in a pressurized steel vessel which contained a glass vial (FIG. 2). The liquid displayed two-layers with the top being the hydrocarbon phase and the bottom the aqueous phase. These were separated manually, volume and mass recorded, and the hydrocarbon phase analyzed by GC-MS and the data collected in Table 2.

Catalyst Characterization

Although the properties of the silica support from Saint-Gobain were reported, independent BET measurements of surface area, pore volume, and pore diameter were made.

BET (Brunauer-Emmett-Teller) or Surface Area and Porosity Measurements

The $SiO_2$ support was prepared by using the sample degas machine (micromeritics, FlowPrep 600) to clear out the air and moisture content inside the support pores. After that, the surface area, pore volume, and the pore size of the $SiO_2$ support was determined by using the BET surface analysis (micromeritics, TriStar II) as shown in Table 1.

TABLE 1

| Characterization of Saint-Gobain Silica Support | |
| --- | --- |
| Catalyst support property | $SiO_2$ |
| Pellet diameter (mm) | 3 |
| Surface area (m²/g) | 210 |
| Pore volume (m³/g) | 1.5 |
| Average pore diameter (Å) | 105 |

TPR (Temperature Programmed Reduction)

The calcined but not reduced catalyst UTA-1 was examined by temperature programmed reduction (TPR) to determine the temperature at which the precatalyst should be reduced and the behavior of the reduction process. TPR was obtained by running a thermogravimetric analysis (TGA) versus temperature in a reducing atmosphere. The TGA was performed on crushed, powdered pellets in a TA instrument, SDQ600 in which the flowing gas was composed of 3% $H_2$ and 97% $N_2$. The mixed gas flowed at 20 ml/min during the TPR process with the following temperature profile:

Equilibrate at 50° C.
Isothermal for 30 min
Ramp 5° C./min to 100° C.
Ramp 1° C./min to 900° C.

The data from a TPR run is shown in FIG. 3 and indicates two reductive processes at temperatures above ~180° C. The first process may be the reduction of Co(III) oxides to Co(II) oxides and the second process between 260° C. and 320° C. being the reduction to the metal. Previous studies show that the presence of the RuO helps facilitate the reduction of the cobalt oxide at these temperatures. From this data, reduction and activation of the FT catalyst in situ by using temperatures in excess of 320° C. can confidently be run.

SEM (Scanning Electron Microscopy) and TEM (Transmission Electron Microscopy)

SEM is used to image the microscopic and nanoscopic surface structure and morphology of the catalyst pellet. TEM provides similar data but also provides crystallographic information. As seen in the SEM FIGS. 4A and 4B, the catalyst is composed of small spheres and fused clumps of spheres with a relatively narrow size distribution which ranges between 0.4 µm to 2 µm for reduced catalyst. However, the catalyst showed significantly increase of support size to 1 µm to 4 µm after the synthesis (FIG. 4B). Similar to the cobalt particle size from the TEM images shown in FIGS. 4C and 4D, is at greater magnification and shoes 5-10 nm sized cobalt particles on the surface of the larger silica particles. In FIG. 4C, the cobalt particle are uniformly distributed over $SiO_2$ support after reduced in the $H_2$ gas at 100 sccm flow rate 400° C. at atmospheric pressure for 18 h. As a result of the synthesis, the cobalt particles started to sinter and formed larger cobalt particle size (50-100 nm) as shown in FIG. 4D which cause an early deactivation of the FT catalyst.

FTS Data

Figure 5:
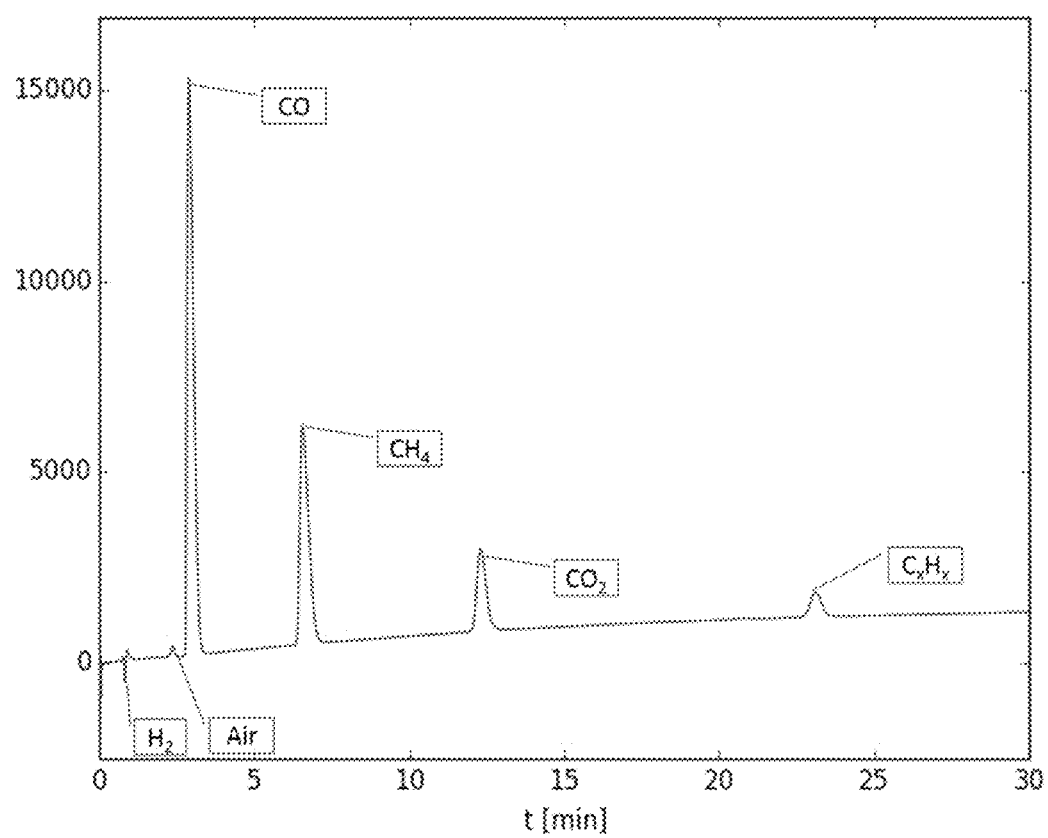
FIG. 5 is a gas chromatogram (GC) of the gas product.

The FTS performance of catalyst UTA-1 was followed by periodically obtaining a gas chromatographic analysis of the tail gas and tracking the outlet gas flow rate. The water and liquid hydrocarbon products are continuously collected in a pressurized collection flask, and can only be examined in aggregate post run. FIG. 5 shows a typical gas chromatogram (GC) and indicates the presence of $H_2$, $N_2$, CO, $CO_2$, $CH_4$ and other light hydrocarbons. Peak area is proportional to product quantity and quantitative analysis of the various products and by-products obtained. The gas products were determined every hour after the synthesis starts by using the GC from SRI Instruments (SRI 8610C, ShinCarbon). These data not only show the amounts and types of molecules coming off the FTS process but also how they evolve with time.

Figure 6:
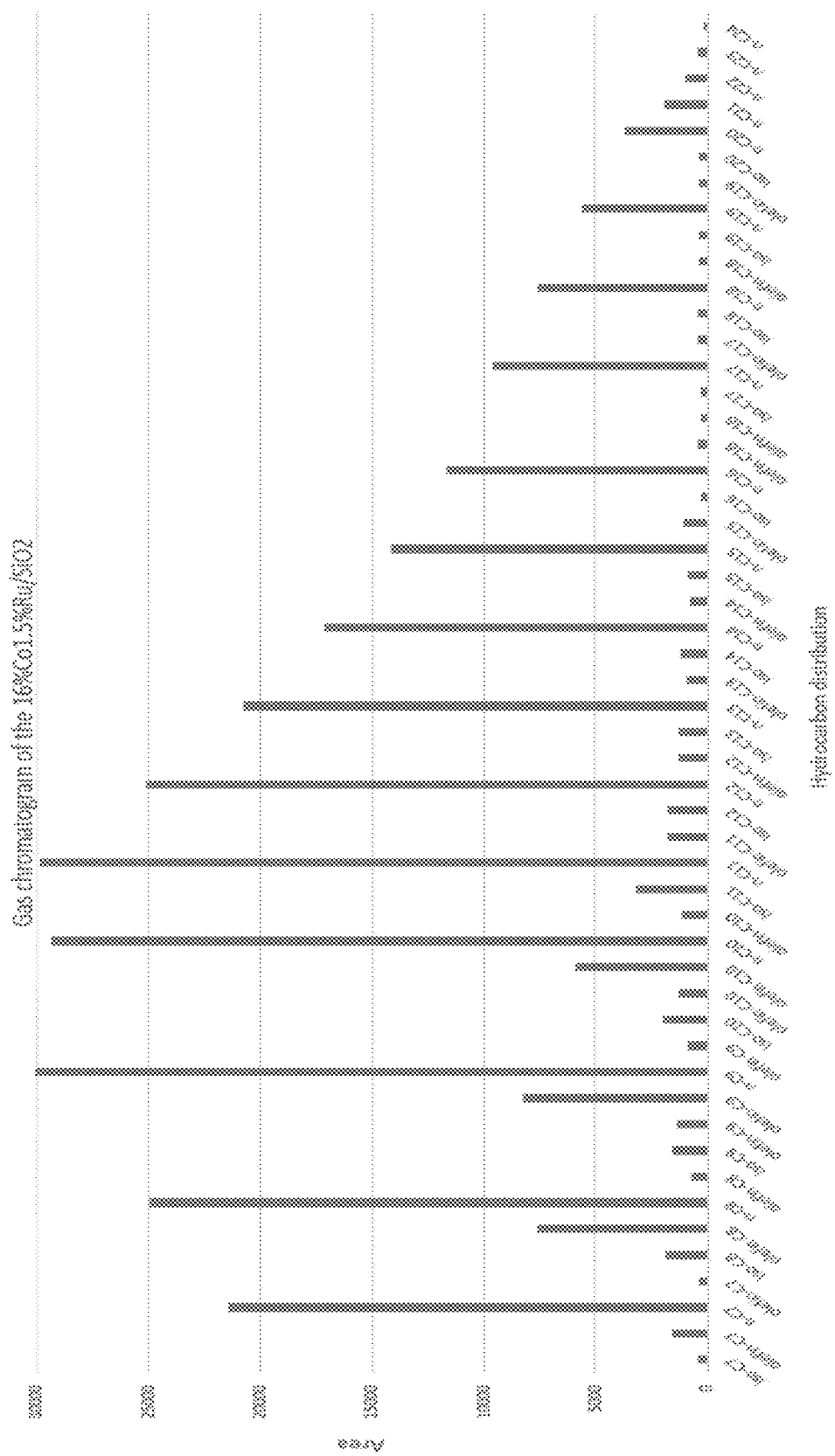
FIG. 6 is a gas chromatogram of oil product from catalyst UTA-1 (16% Co1.5% Ru/SiO$_2$) showing the hydrocarbon distribution in the range of $C_7$ to $C_{24}$.

After a FTS run, the oil product is measured and analyzed by GC from SRI instrument (SRI 8160C, Capillary column) to see the carbon distribution and quantification (FIG. 6.). According to the gas chromatogram shown in FIG. 6, the $C_{6-14}$ are the major hydrocarbon produced in the FTS and most of the hydrocarbon are straight chain or paraffin (about 82% of the total weight of the oil).

TABLE 2

Fischer-Tropsch synthesis operating condition and product characterization

| Catalyst type (% wt) | 16% Co1.5% Ru/SiO$_2$ |
|---|---|
| Operating condition | |
| Reduction temperature (° C.) | 400 |
| Activation temperature (° C.) | 255 |
| Flow rate (sccm) | 100 |
| H$_2$/CO molar ratio | 2 |
| Feed type | Commercial syngas (Airgas) |
| Time on Steam (h) | 143 |
| Pressure (Psig) | 300 |
| Productivity | |
| Catalyst productivity (mg$_{oil}$/g$_{cat}$·h) | 68.18 |
| Oil (g) | 19.5 |
| Water (g) | 93.49 |
| Alcohol (g) | 3.41 |
| Wax (g) | 0 |
| Selectivity | |
| Oil (% mass) | 10.93 |
| CH$_4$ (% mass) | 34.43 |
| Water (% mass) | 52.66 |
| Alcohols (% mass) | 3.52 |
| Syngas conversion (%) | 43.45 |
| Product distribution | |
| Oil (C$_{5+}$ hydrocarbon) | |
| Maximum carbon number | 24 |
| Isomer (% mass) | 5.21 |
| n-product (paraffins) (% mass) | 82.78 |
| Olefin (% mass) | 12.01 |
| Alcohol | |
| Methanol (% mass) | 1.28 |
| Ethanol (% mass) | 1.27 |
| 1-Propanol (% mass) | 0.4 |
| 1-Butanol (% mass) | 0.3 |
| 1-Pentanol (% mass) | 0.19 |
| 1-Hexanol (% mass) | 0.08 |

Example 2

Described herein is an embodiment of the method of production for an embodiment of a catalyst for Fischer-Tropsch synthesis. The embodiment of the method as described herein is similar for that as described in Example 1, however, the catalyst can be dried with nitrogen rather than air.

Catalyst UTA-2 Preparation

1. Commercial silica oxide support (6 g) was pretreated in the degas machine to clear out air and moisture inside the catalyst pores. The catalyst was loaded into the test tube about 2 inches long and the tube was sealed with plastic stopper at the top. The gas needle and the exhaust needle are inserted into the stopper as shown in FIG. 7. Nitrogen gas (N$_2$) was fed into the tube from the gas needle with gas flow rate 5 sccm. The SiO$_2$ was heated to 120° C. under nitrogen gas flow for about 12-18 h. (overnight).

2. The cobalt nitrate (Co(NO$_3$)$_2$·6H$_2$O, Alfa Aesar) was prepared with 16% metal content on silica oxide support (0.98 g$_{cobalt\ nitrate}$ g$_{SiO2}$) The cobalt nitrate was dissolved in DI water (0.76 mL$_{DI\ water}$/g$_{SiO2}$) IWI was used to impregnate the SiO$_2$ support by using the cobalt nitrate solution. After the SiO$_2$ support was impregnated, 6 g of precatalyst was packed in the stainless steel tube furnace as shown in FIGS. 8A and 8B with the packing length of 3 inches.

3. The tube furnace was sealed with stainless steel nut connected to the N$_2$ gas line. A thermocouple was inserted from the bottom of the tube furnace which opens to the atmospheric. The heat tape, the heating element of the tube furnace, was connected to the PID controller (Omega CN7500) in order to control and monitor temperature while the catalyst was dried. The tube furnace was rapidly heated up to 110° C. before feeding N$_2$ gas to drying bed. The gas flow rate was maintained at gas hourly space velocity (GHSV) 3,000 h$^-$ (GHSV is determined from the N$_2$ gas flow rate per catalyst packing volume, hence the N$_2$ flow rate may vary depending on the packing length). The drying was held for 3 h before cooling down while keep the gas flowing.

Figure 9A:
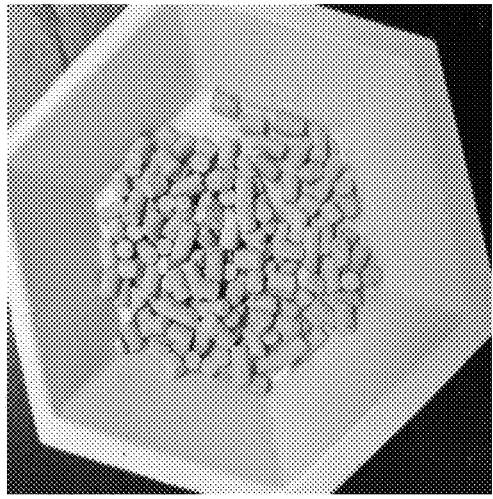
FIG. 9A-9B are photographs showing liquid synthesis catalyst UTA-2 during preparation process.

4. The catalyst was unpacked and transferred from the tube furnace into the ceramic crucible (FIG. 9A). The catalyst was calcined in the temperature programmed oven with the following temperature ramping profile:

Temp.$_{25°\ C.}$-Temp$_{100°\ C.}$ Ramping 10° C./min
Temp.$_{100°\ C.}$ Hold for 30 min
Temp.$_{100°\ C.}$-Temp.$_{400°\ C.}$ Ramping 10° C./min
Temp.$_{400°\ C.}$ Hold for 5 h.

Figure 9B:
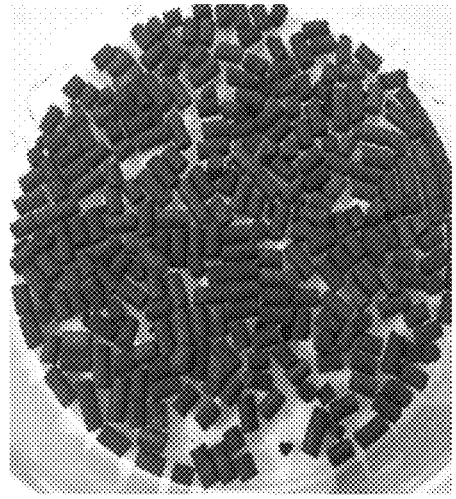

During the calcination process, air was fed into the temperature programmed oven from the top side to help eliminate the nitrate content in the cobalt catalyst. The catalyst after calcination is shown in FIG. 9B.

In Situ Reduction and Use of the UTA-2 FT Catalyst:

The calcined catalyst was tested in the FTS to measure the selectivity and productivity. The catalyst was diluted by using quartz chips with the ratio 2 g catalyst/2.76 g quartz chip before packing into ⅜ inch diameter stainless reactor. Steel wool was used to hold the catalyst bed to stay in the oven zone. The catalyst was reduced at 400° C., atmospheric pressure, and hydrogen flow rate of 100 sccm for 18 h before switching to the activation process. In this phase, the reactor is cooled to 150° C. and purged with H$_2$ at a steady flow rate 100 sccm while the pressure is slowly raised to 300 psig. Once the desired pressure is obtained, the gas feed is switched to a mixture of H$_2$ at a flow rate of 66.6 sccm and CO at a flow rate of 33.3 sccm. The flow rate between H$_2$ and CO was kept constant at the ratio 2 to keep the molar H$_2$ to CO ratio at 2.0. Once the flow rate between H$_2$ and CO was stable, the temperature was brought up slowly (heating rate 0.6° C./min) to the desired temperature, which can range from 220° C. to 260° C. A temperature of 255° C. was common for many of the runs. Temperature, inlet, and outlet flow rate, and gas products activity were monitored at all time during the synthesis.

Figure 10A:
FIGS. 10A-10B are photographs showing the liquid products collected from the gas-liquid separator and liquid collector pressure vessel.
Figure 10B:

Once the temperature point is achieved and the pressure and flow rates stable, the run was considered started. In general, the FTS run lasted 5-7 days before it was shut down. The liquid product in the gas-liquid separator and liquid collector pressure vessel was separated (FIGS. 10A and 10B) and analyzed (Table 4).

Catalyst Characterization $SiO_2$ support and FT catalyst were tested by using the following instrument.

BET (Brunauer-Emmett-Teller) or Surface Area and Porosity Measurements

The $SiO_2$ support was prepared by using the sample degas machine (micromeritics, FlowPrep 600) to clear out the air and moisture content inside the support pores. After that, the surface area, pore volume, and the pore size of the $SiO_2$ support was determined by using the BET surface analysis (micromeritics, TriStar II) as shown in Table 3.

TABLE 3

Characterization of $SiO_2$ support from Saint-Gobain

| Catalyst support property | $SiO_2$ |
|---|---|
| Pellet diameter (mm) | 3 |
| Surface area (m²/g) | 210 |
| Pore volume (m³/g) | 1.5 |
| Average pore diameter (Å) | 105 |

TPR (Temperature Programmed Reduction)

Temperature Programmed Reduction or TPR was used to determine the degree of reduction and reduction temperature of the catalyst after fabricated. The TPR was done by using the Thermogravimetric Analysis (TGA, TA instrument, SDQ600) under the mixed gas between 3% $H_2$ and 97% $N_2$. The crush catalyst sample was thermally analyzed in the TPR and interpreted as shown in FIG. 11. The graph from TPR showed suitable reduction temperature of the catalyst is at 450° C.

SEM (Scanning Electron Microscopy) and TEM (Transmission Electron Microscopy)

Scanning Electron Microscopy (SEM) is the technique that used to analyze surface structure and morphology of the catalyst pellet in the micro- and nanometer scale size. Similar to Transmission Electron Microscopy (TEM) which provides the morphologic composition and the crystallographic information. By using the TEM, nano-scale distribution can be observed. FIGS. 12A and 12B showed the cobalt distribution between the 16% $Co/SiO_2$ with air dry and $N_2$ dry. The catalyst with the $N_2$ dry (FIG. 12B) showed more dispersion of the cobalt particles over the SiO2 support than the catalyst with the air dry (FIG. 12A).

FTS Data

Figure 13:
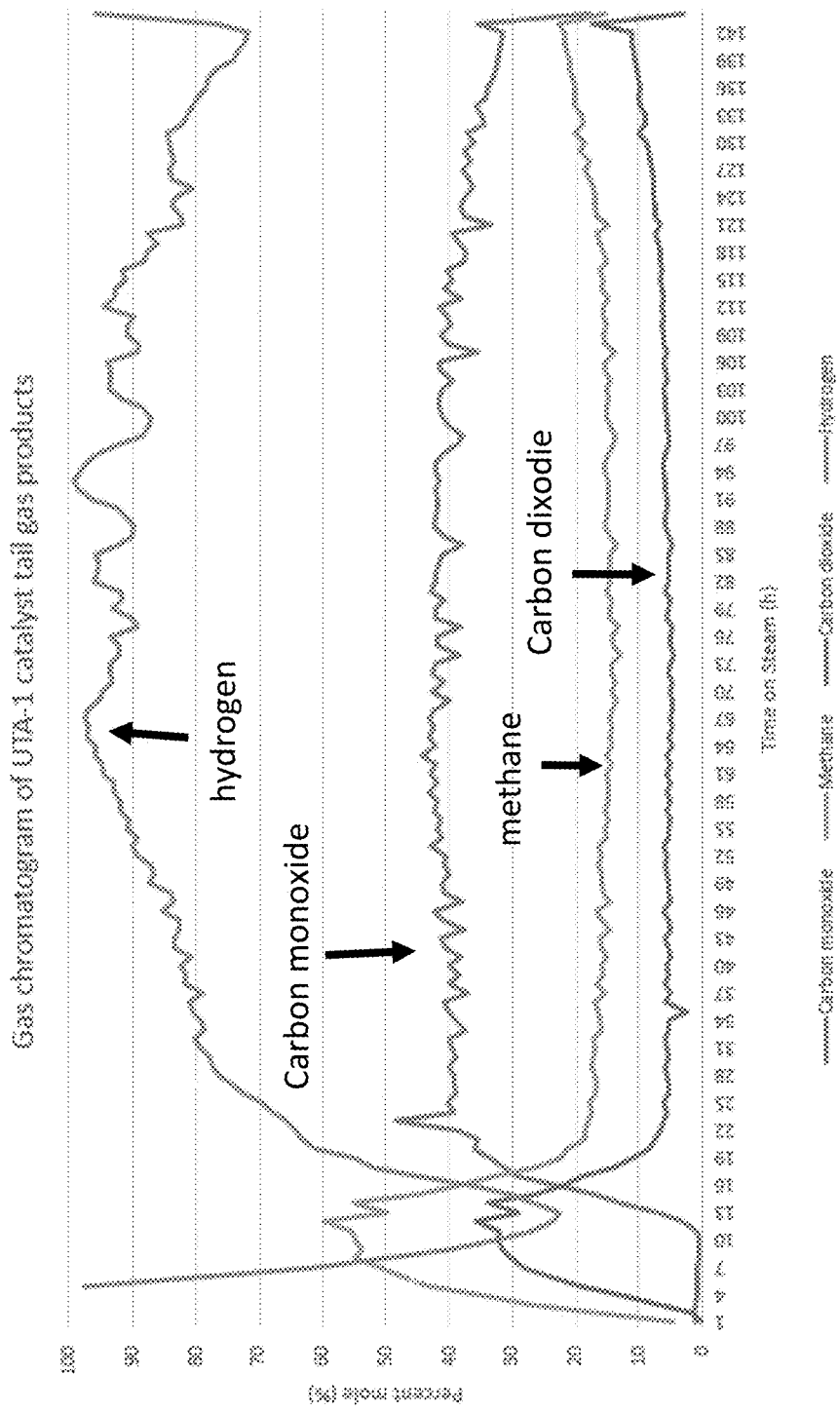
FIG. 13 is a gas chromatogram of tail gas from catalyst UTA-2 (16% Co/SiO$_2$ with nitrogen dry) showing gas composition of percent mole as a function of time.

The FTS performance of catalyst UTA-2 was tracked by periodically obtaining a gas chromatographic analysis of the tail gas and monitoring the outlet gas flow rate. The water and liquid hydrocarbon products are continuously collected in a pressurized collection flask, and can only be examined in aggregate post run. FIG. 13 shows the percent mole of tail gas composition as a function of time which composes of the $H_2$, CO, $CH_4$, and $CO_2$. The gas products were determined every hour by using the GC from SRI Instruments (SRI 8610C, ShinCarbon). The chromatogram was analyzed and plotted to indicate the activity and productivity of the synthesis. As a result shown in FIG. 13, $CH_4$ and $CO_2$ showed high activity in the first 24 h after the synthesis started which showed the large consumption of the syngas ($H_2$ and CO). After the synthesis stabilize, the amount of $H_2$ start to increase which might came from the side reaction of the FT synthesis.

Figure 14:
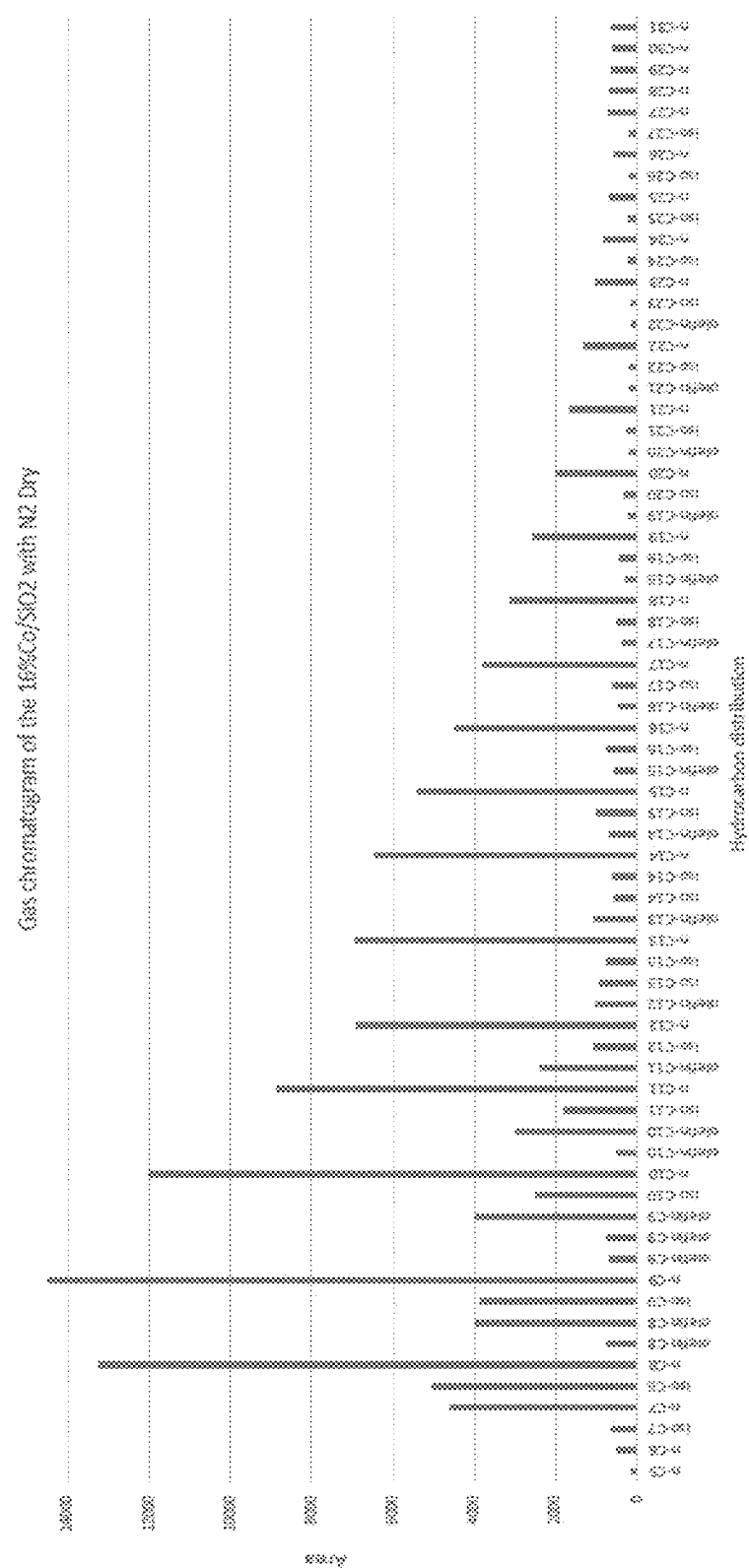
FIG. 14 is a gas chromatogram of oil product from catalyst UTA-2 (16% Co/SiO$_2$ with nitrogen dry) showed the hydrocarbon distribution in the range of $C_5$ to $C_{31}$.

After the FTS run, the oil product is measured and analyzed by GC from SRI Instrument (SRI 8610C, Capillary column) to see the distribution and quantify hydrocarbon of the oil product. The hydrocarbon chain from $C_5$ to $C_{31}$ were produced from UTA-2 catalyst as shown in FIG. 14 which about 3 times higher isomer than the UTA-1 catalyst oil product as well as the alcohol.

TABLE 4

Fischer-Tropsch synthesis operating condition and product characterization

| Catalyst type (% wt) | 16% $Co/SiO_2$ ($N_2$ dry) |
|---|---|
| Operating condition | |
| Reduction temperature (° C.) | 400 |
| Reaction temperature (° C.) | 255 |
| Flow rate (sccm) | 100 |
| $H_2$/CO molar ratio | 2 |
| Feed type | Commercial syngas (Airgas) |
| Time on Steam (h) | 141 |
| Pressure (Psig) | 300 |
| Productivity | |
| Catalyst productivity ($mg_{oil}/g_{cat}$·h) | 69.78 |
| Oil (g) | 19.48 |
| Water (g) | 72.19 |
| Alcohol (g) | 15.85 |
| Wax (g) | 0.2 |
| Selectivity | |
| Oil (% mass) | 13.01 |
| $CH_4$ (% mass) | 28.05 |
| Water (% mass) | 48.21 |
| Alcohols (% mass) | 10.58 |
| Syngas conversion (%) | 37.17 |
| Product distribution | |
| Oil ($C_{5+}$ hydrocarbon) | |
| Maximum carbon number | 31 |
| Isomer (% mass) | 15.42 |
| n-product (paraffins) (% mass) | 70.28 |
| Olefin (% mass) | 14.29 |
| Alcohol | |
| Methanol (% mass) | 5.74 |
| Ethanol (% mass) | 7.43 |
| 1-Propanol (% mass) | 2.83 |
| 1-Butanol (% mass) | 1.15 |
| l-Pentanol (% mass) | 0.75 |
| l-Hexanol (% mass) | 0.13 |

Example 3

Figure 15:
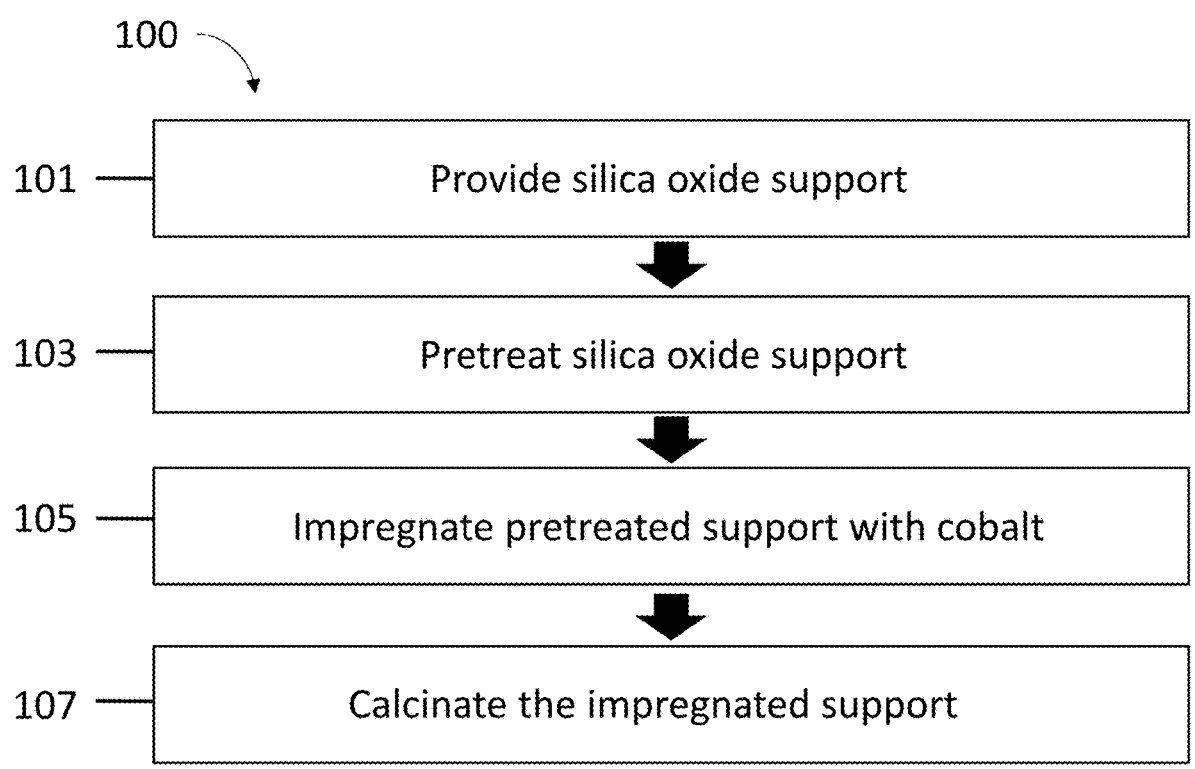
FIG. 15 is a flowchart illustrating an embodiment of a method according to the present disclosure.

FIG. 15 is a flow chart illustrating an embodiment of a method 100 according to the present disclosure. According to the embodiment of the method 100, a silica oxide support is provided 101, which is pretreated 103, impregnated with cobalt from a cobalt source 105, and calcinated (aka calcined) 107. The impregnated support 105 can also be dried in the presence of air or nitrogen at a temp of about 90° C. to about 130° C.

Example 4

Figure 16:
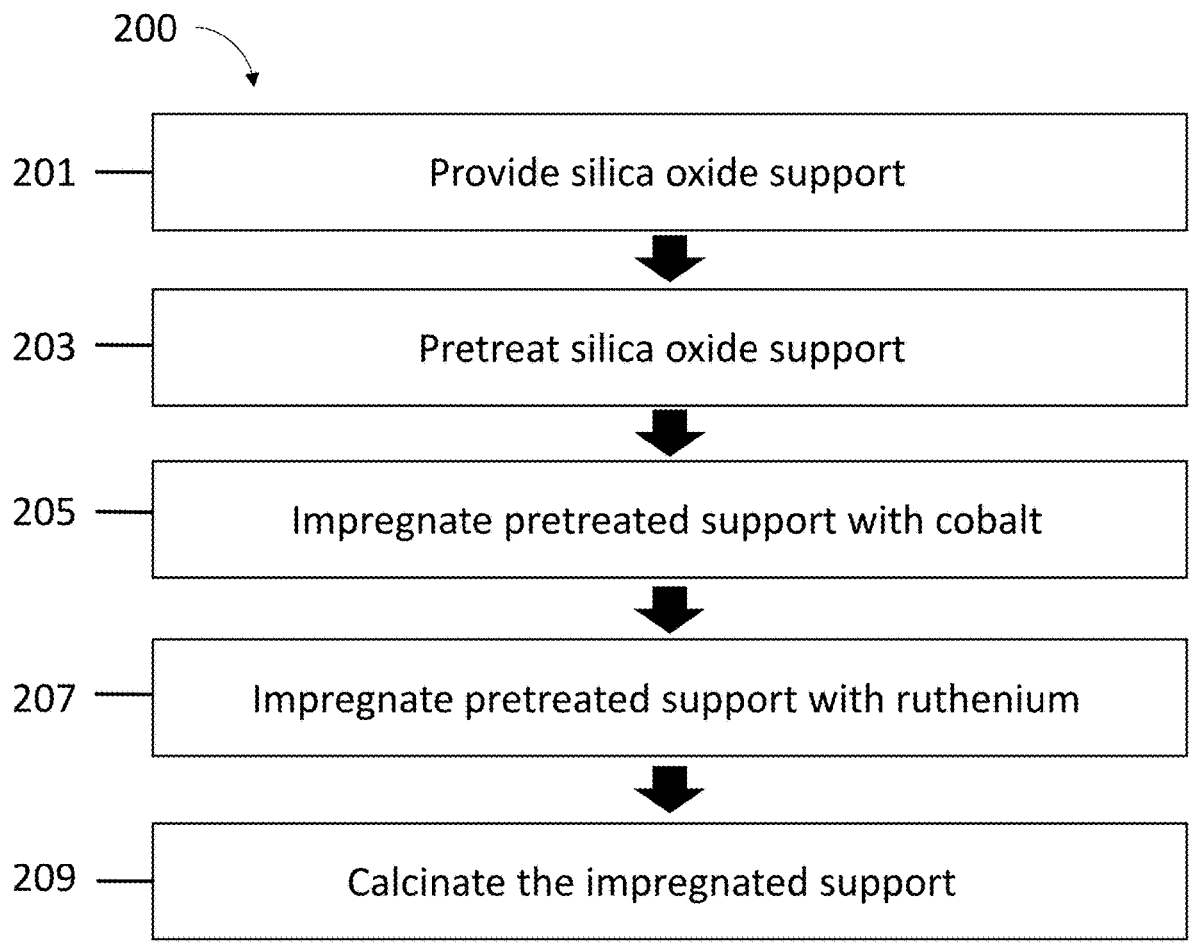
FIG. 16 is a flowchart illustrating an embodiment of a method according to the present disclosure.

FIG. 16 is a flow chart illustrating an embodiment of a method 200 according to the present disclosure. According to the embodiment of the method 200, a silica oxide support is provided 201, which is pretreated 203, impregnated with cobalt from a cobalt source 205, impregnated with ruthenium from a ruthenium source 207, and calcinated (aka calcined) 209. The impregnated support 205 and 207 can also be dried in the presence of air or nitrogen at a temp of about 90° C. to about 130° C. after cobalt impregnation 205 and separately after ruthenium impregnation 207.

Example 5

Figure 17:
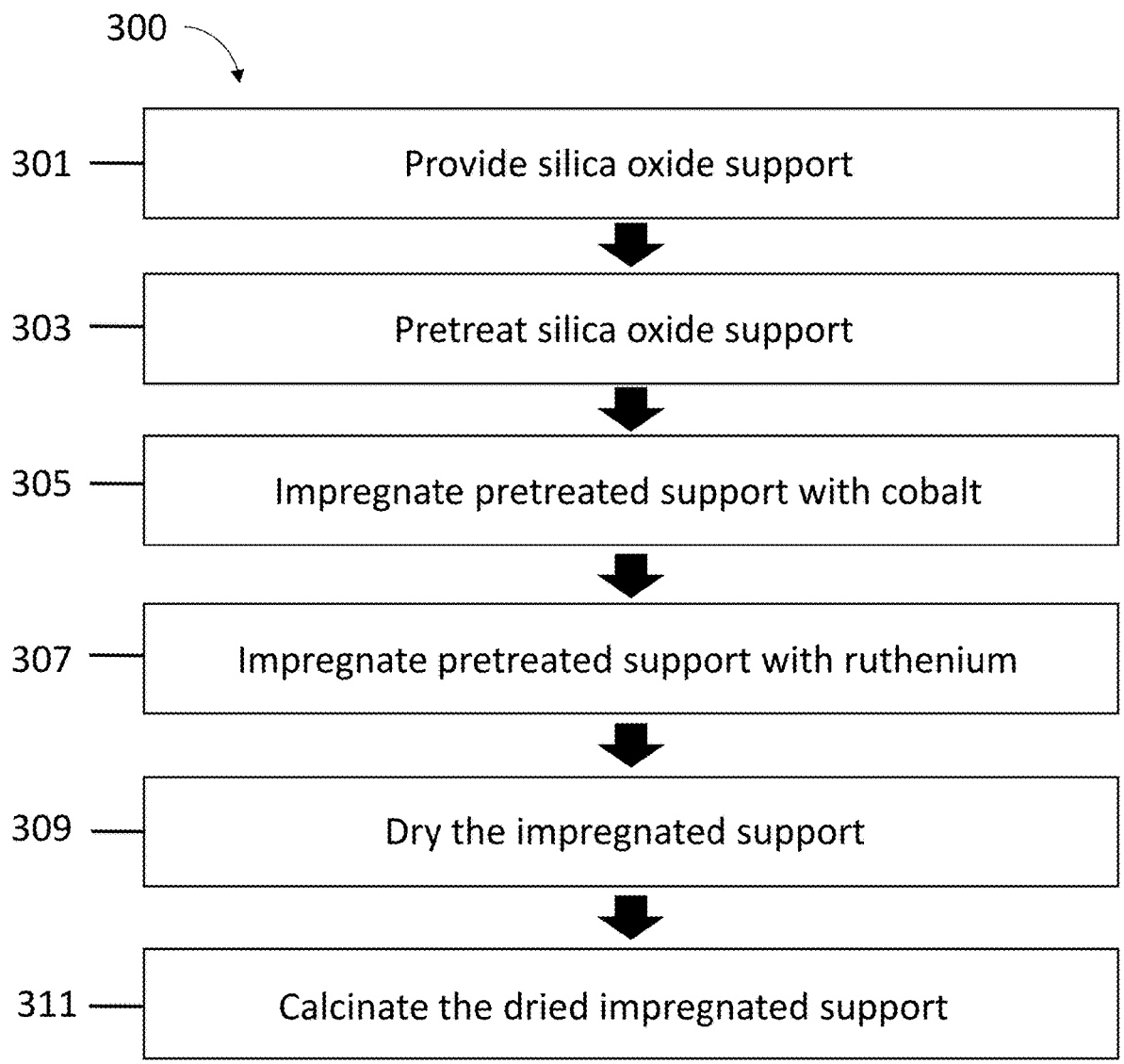
FIG. 17 is a flowchart illustrating an embodiment of a method according to the present disclosure.

FIG. 17 is a flow chart illustrating an embodiment of a method 300 according to the present disclosure. According to the embodiment of the method 300, a silica oxide support is provided 301, which is pretreated 303, impregnated with cobalt from a cobalt source 305, impregnated with ruthenium from a ruthenium source 307, and calcinated (aka calcined) 311. The impregnated support 305 and 307 can also be dried 309 in the presence of air or nitrogen at a temp of about 90° C. to about 130° C. after cobalt impregnation 305 and separately after ruthenium impregnation 307.

Example 6

Figure 18:
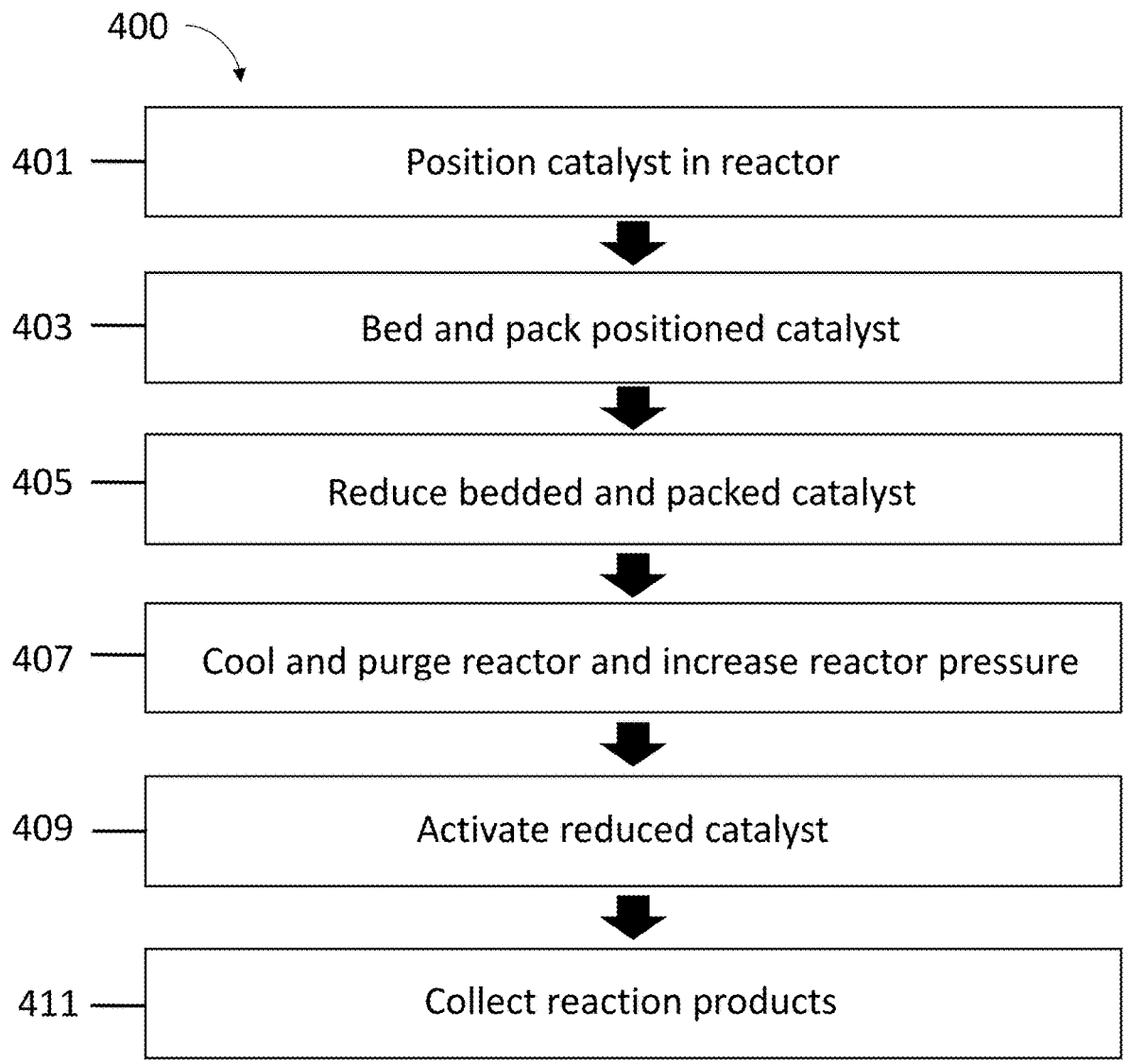
FIG. 18 is a flowchart illustrating an embodiment of a method according to the present disclosure.

FIG. 18 is a flow chart illustrating an embodiment of a method 400 according to the present disclosure. According to the embodiment of the method 400, liquid synthesis catalyst according to the present disclosure is positioned in a reactor 401. The positioned catalyst is bedded and packed in the reactor 403, and then reduced 405 with a gas, for example $H_2$ gas. Following catalyst reduction 405, the reactor is cooled and the gas purged and the reactor pressure is increased to a set reactor pressure 407. The reduced catalyst is then activated 409, and the reaction products collected 411.

Example 7

Figure 19:
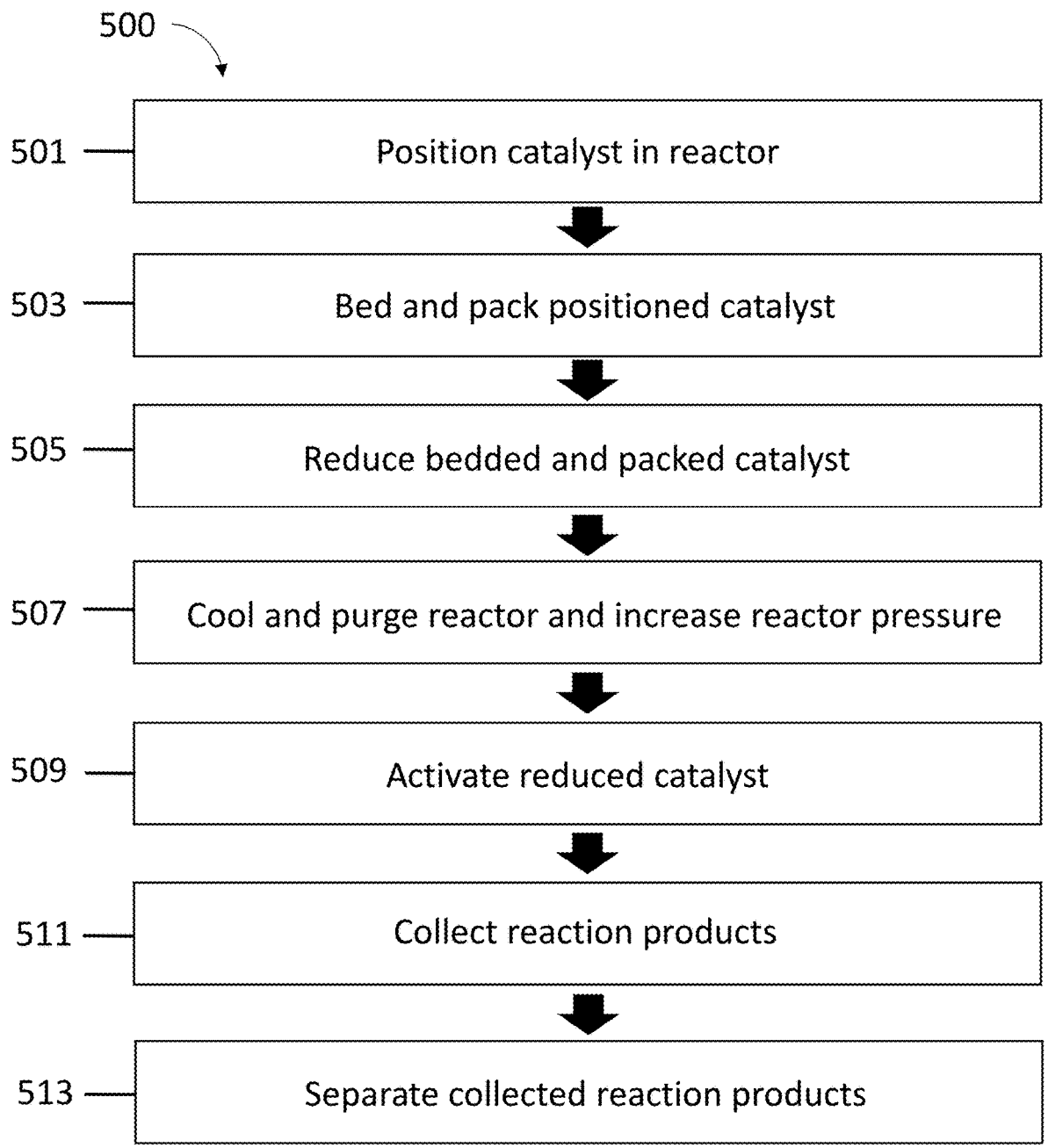
FIG. 19 is a flowchart illustrating an embodiment of a method according to the present disclosure.

FIG. 19 is a flow chart illustrating an embodiment of a method 500 according to the present disclosure. According to the embodiment of the method 500, liquid synthesis catalyst according to the present disclosure is positioned in a reactor 501. The positioned catalyst is bedded and packed in the reactor 503, and then reduced 505 with a gas, for example $H_2$ gas. Following catalyst reduction 505, the reactor is cooled and the gas purged and the reactor pressure is increased to a set reactor pressure 507. The reduced catalyst is then activated 509, and the reaction products collected 511 and separated 513.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

All publications and patents cited in this specification are incorporated by reference as if each individual publication or patent were specifically and individually indicated to be incorporated by reference and are incorporated by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could differ from the actual publication dates that may need to be independently confirmed.

Therefore, the following is claimed:

1. A method of producing a liquid synthesis catalyst, said method comprising the steps of:
   impregnating a silica oxide support with cobalt;
   drying the cobalt-impregnated silica oxide support with an inert gas; and
   after drying with the inert gas, calcinating the cobalt-impregnated silica oxide support in the presence of oxygen to produce a liquid synthesis catalyst.

2. The method of claim 1, wherein the silica oxide support comprises silica oxide pellets.

3. The method of claim 2, wherein the silica oxide pellets are cylindrical and have a dimension of about 2 mm to about 4 mm.

4. The method of claim 2, wherein the silica oxide pellets have a packing density of about 20 lbs/ft$^3$ to about 40 lbs/ft$^3$.

5. The method of claim 1, wherein the cobalt is sourced from cobalt nitrate or cobalt chloride.

6. The method of claim 1, wherein the silica oxide support is impregnated with cobalt by incipient wet impregnation (IWI).

7. The method of claim 1, further comprising the step of impregnating the cobalt-impregnated silica oxide support with ruthenium before the drying step.

8. The method of claim 7, wherein the cobalt-impregnated silica oxide support is impregnated with ruthenium by incipient wet impregnation (IWI).

9. The method of claim 7, wherein the ruthenium is sourced from ruthenium chloride or ruthenium nitrate.

10. The method of claim 1, wherein the step of drying the cobalt-impregnated silica oxide support comprises drying the cobalt-impregnated silica oxide support with an inert gas at a temperature of about 90° C. to about 130° C.

11. The method of claim 1, wherein the inert gas is $N_2$ gas.

12. The method of claim 1, further comprising the step of removing air and moisture from pores of the silica oxide support by pretreating the silica oxide support at a temperature of about 90° C. to about 120° C., wherein the pretreating step is done before the step of impregnating the silica oxide support with cobalt.

13. The method of claim 12, wherein the pretreating step is done in the presence of an inert gas.

14. The method of claim 13, wherein the inert gas is $N_2$ gas.

15. The method of claim 1, wherein the cobalt-impregnated silica oxide support is calcinated in an oven, wherein the calcinating step comprises feeding air into the oven.

16. The method of claim 1, wherein the cobalt-impregnated silica oxide support is calcinated in an oven with a temperature ramping profile, wherein the temperature ramping profile comprises:
   ramping from a temperature of about 25° C. to about 100° C. at a rate of about 10° C./minute;
   holding at a temperature of about 100° C. for about 30 minutes;
   ramping from a temperature of about 100° C. to about 400° C. at a rate of about 10° C./minute; and
   holding at a temperature of about 400° C. for about 5 hours.

17. The method of claim 16, wherein the calcinating step comprises feeding air into the oven.

* * * * *